(12) United States Patent
Hagedorn

(10) Patent No.: US 6,841,363 B2
(45) Date of Patent: Jan. 11, 2005

(54) PREPARATION OF CAPPED MRNA

(75) Inventor: Curt H. Hagedorn, Atlanta, GA (US)

(73) Assignee: Emory University, Atlanta, GA (US)

( * ) Notice: Subject to any disclaimer, the term of this patent is extended or adjusted under 35 U.S.C. 154(b) by 84 days.

(21) Appl. No.: 09/957,689

(22) Filed: Sep. 19, 2001

(65) Prior Publication Data

US 2002/0042502 A1 Apr. 11, 2002

Related U.S. Application Data

(60) Provisional application No. 60/233,677, filed on Sep. 19, 2000.

(51) Int. Cl.$^7$ ................................................. C12P 19/34
(52) U.S. Cl. ................ 435/91.1; 435/91.21; 435/91.51; 435/6; 435/DIG. 37; 536/23.1
(58) Field of Search .............................. 435/91.1, 91.21, 435/91.51, 6, DIG. 37; 536/23.1

(56) References Cited

U.S. PATENT DOCUMENTS 6,232,442 B1    5/2001  Hagedorn et al. .......... 530/350

FOREIGN PATENT DOCUMENTS

| WO | WO 98/28325 | 2/1998 | ............ C07K/1/22 |
|---|---|---|---|
| WO | WO 98/08865 | 3/1998 | |

OTHER PUBLICATIONS

Laurino et al, Molecular and Cellular biology, (1/99), 19(1), 173–181.*
Edery, I. et al. (1995) *Mol. Cell. Biol.* 15:3363–3371.
Altmann et al. (1998) *Gene* 74:517–525.
Haas, D.W. et al. (1991) *Arch. Biochem. Biophys.* 284:84–89.
Hsu, P.–C. et al. (2000) *Biochemistry* 39:13730–13736.
Reychlik, W. et al. (1987) *Proc. Natl. Acad USA.* 84:945–949.
Supplementary European Search Report, Jun. 17, 2004, pp. 1–3.

* cited by examiner

Primary Examiner—T. D. Wessendorf
(74) Attorney, Agent, or Firm—Greenlee Winner and Sullivan, P.C.

(57) ABSTRACT

The invention provides a process for preparing capped mRNAs from an RNA mixture, e.g. whole RNA isolated from a cell or tissue extract, that includes combining in a reaction mixture RNA comprising capped mRNA with a separable affinity matrix having high-affinity eIF4E bound thereto, under conditions sufficient for binding to occur between the high-affinity eIF4E and the capped mRNA, whereby capped mRNA is bound to the affinity matrix, separating the affinity matrix from the reaction mixture, then separating the capped mRNA from the affinity matrix. High affinity eIF4E mutants previously described are employed in the process as well as a novel mutant disclosed and claimed herein. The mRNA preparation process is based on isolation of 5'-capped mRNA. The mRNA molecules thus isolated have intact sequences encoding the $NH_2$-terminal ends of the proteins they encode, unlike those isolated by prior methods. In addition, use of the method isolates mRNA sequences not isolatable by prior methods that relied on binding to polyadenylated 3'-end sequences.

5 Claims, 6 Drawing Sheets

|  | Oligo (dT) column | GST-4Ek119A batch |
|---|---|---|
| Starting material (Total RNA) | 1 mg | 1 mg |
| Average quantity of mRNA recovered | 1.4 ug | 4.3 ug |

FIG. 3B

PREPARATION OF CAPPED MRNA

CROSS REFERENCE TO RELATED APPLICATIONS

This application claims the benefit of U.S. Provisional Application Ser. No. 60/233,677 filed Sep. 19, 2000.

ACKNOWLEDGMENT OF FEDERAL RESEARCH SUPPORT

Support for research leading to the invention was provided in part by the National Institutes of Health Grant No. CA63640. The United States Government has certain rights in the invention.

BACKGROUND OF THE INVENTION

The present invention relates to isolation of messenger RNA (mRNA) from cells and tissues, preparation of cDNA, mRNA libraries and cDNA libraries. All available cDNA libraries to date have been constructed from polyadenylated RNA, on the premise that the majority of mRNA sequences are polyadenylated. Polyadenylated mRNA has typically been isolated by chromatography on oligo(dT). However, two problems have had to be faced by workers seeking to clone and sequence cDNA. The first stems from the fact that polyadenylation occurs at the 3'-ends of RNA and that the 5' terminal sequences are frequently absent from mRNA and cDNA libraries and are often difficult to obtain even by supplementary means. The second, less obvious problem, is that a significant fraction of mRNAs in a cell at any given time might include mRNAs that are not polyadenylated. The possibility that many mRNAs were simply missed by oligo (dT) isolation has now been confirmed by the results presented herein. The present invention provides methodology for solving both problems, by isolating mRNA based on a common feature of the 5' end, the $m^7G$ cap.

Studies of the process of protein synthesis in eukaryotic cells have shown that initiation of translation (the process of protein synthesis based on sequence information of the mRNA) requires molecular modification of the 5' end of mRNA. The modifications include the covalent addition of a "cap" of 7-methylguanosine diphosphate ($m^7GDP$) to the 5' end of mRNA, and the subsequent non-covalent binding of a complex of initiation factors. Watson, J. D. et al. *Molecular Biology of the Gene*, 4$^{th}$ ed. p. 569 Benjamin, Menlo Park, 1987. The primary component involved in the binding of initiation factors to the capped mRNA is the protein designated eIF4E (initiation factor 4E), which binds directly to the $m^7GDP$ of the mRNA cap and then functions to facilitate the binding of other protein initiation factors.

The eIF4E protein has been cloned, sequenced, expressed and purified. Its binding to the cap structure has been studied in detail. Variant structures (mutants) having single amino acid substitutions, have been synthesized; having either enhanced or reduced binding affinity for the $m^7G$ cap structure (U.S. Pat. No. 6,232,442). It is clear from a biological perspective that the binding affinity of eIF4E for capped mRNA is a significant factor regulating the rate of protein synthesis in cells. The present invention is a practical application of eIF4E variants having enhanced binding affinity for capped mRNA.

Prior attempts to employ eIF4E as a binding agent to isolate capped mRNA have been reported [Edery (1995) *Mol. Cell. Biol.* 15:3363–3371]. However, the yield was low, probably because high-affinity eIF4E was not known at the time the work was reported. As a result the binding was less efficient, as comparative studies described herein have shown, and column chromatography was required to effect purification. No comparison with the oligo(dT) method was reported and no follow-up studies have been reported.

The sequence of DNA encoding human eIF4E has been determined [Reychlik, W. et al. (1987) *Proc. Natl. Acad. USA* 84:945–949]. Yeast eIF4E and a fusion protein of mouse eIF4E have been expressed in *E. coli* [Edery, I., et al. (1998) *Gene* 74:517–525; Edery, I., et al. (1995) *Mol. Cell. Biol.* 15:3363–3371]. Haas, D. W. et al. (1991) *Arch. Biochem. Biophys.* 284:84–89 reported purification of native eIF4E from erythrocytes. Stern, B. D. et al. (1993) reported isolation of recombinant eIF4E using denaturing concentrations of urea.

The co-crystal structure of eIF4E with $m^7GDP$ suggests that eIF4E binds to the 5' cap mRNA with a $\pi$—$\pi$ stacking interaction between two tryptopan residues, sandwiching the $m^7G$ base as well as hydrogen bonds between base and acidic protein side chains. Using site-directed mutagenesis on eIF4E, a $\pi$—$\pi$ stacking interaction between two tryptopan residues (Trp-56/Trp-102) and $m^7GTP$ was demonstrated. Additionally, Glu-103 in eIF4E is required for hydrogen bonding to $m^7G$. The $m^7GTP$ binding site in mammalian eIF4E resides along the S1–S2 and S3–S4 loops. Previous photolabeling studies of eIF4E with $[\gamma-^{32}P]$ 8-$N_3GTP$ demonstrated crosslinking at Lys-119 in the S4-H2 loop distant from the $m^7GTP$ binding site. A molecular model based on the cocrystal structure of eIF4E/$m^7GTP$ suggested that 8-$N_3GTP$ binds to a site occupied by the second nucleotide of mRNA.

SUMMARY OF THE INVENTION

The invention provides a process for preparing capped mRNAs from an RNA mixture, e.g. whole RNA isolated from a cell or tissue extract that includes combining in a reaction mixture RNA comprising capped mRNA with a separable affinity matrix having high-affinity eIF4E bound thereto, under conditions sufficient for binding to occur between the high-affinity eIF4E and the capped mRNA, whereby capped mRNA is bound to the affinity matrix, separating the affinity matrix from the reaction mixture, then separating the capped mRNA from the affinity matrix. High affinity eIF4E mutants previously described are employed in the process as well as a novel mutant disclosed and claimed herein. The high-affinity eIF4E proteins were expressed as fusions with glutathione-S-transferase (GST) to facilitate attachment to an affinity matrix, glutathione-agarose. The novel GST—4E fusion proteins are claimed herein as an aspect of the invention. The mRNA preparation process is based on binding to 5'-capped mRNA. The mRNA molecules thus isolated have intact sequences encoding the $NH_2$-terminal ends of the proteins they encode, unlike those isolated by prior methods. In addition, use of the method isolates mRNA sequences not isolatable by prior methods that relied on binding to polyadenylated 3'-end sequences.

Accordingly, the invention provides a novel library of capped mRNA and a novel cDNA library whose members, respectively have different and useful molecular characteristics than those previously available.

The invention also provides diagnostic methods based on detecting and/or measuring the presence of a designated capped mRNA in cell sample. The ability to isolate capped mRNA makes it possible to detect infecting viral mRNA that is not polyadenylated, and also to quantify altered levels of gene expression which are characteristic of certain tumors and certain infections and pathologic states.

DESCRIPTION OF THE DRAWINGS

FIG. 3B is a table comparing the yields of mRNA recovered from different preparation methods, as indicated.

DETAILED DESCRIPTION OF THE INVENTION

Figure 1A:
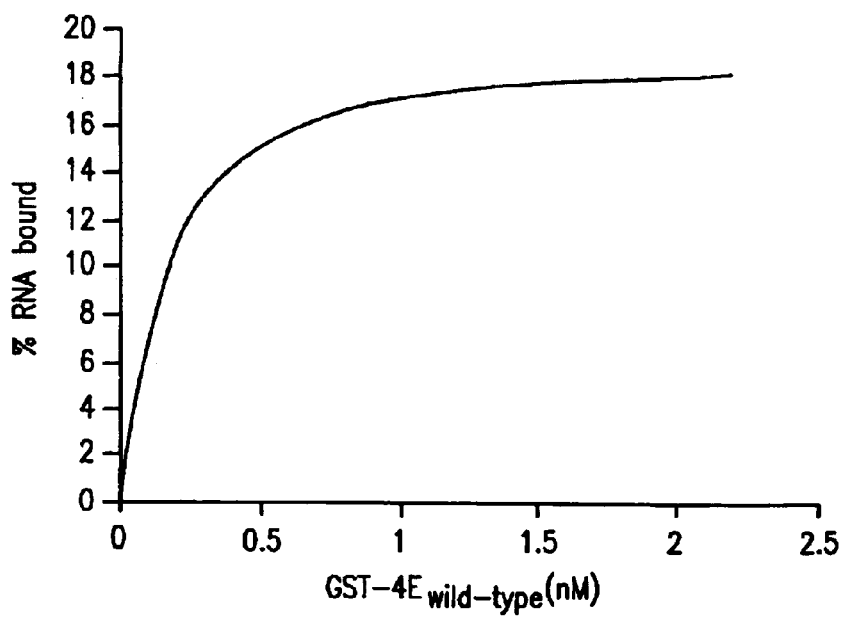
FIG. 1A is a graph of mRNA binding by wild-type GST-4E fusion protein.

The term mRNA is used herein in its usual and customary sense known in the art, which can be ascertained from standard texts. mRNA undergoes co-transcriptional and post-transcriptional modifications which include capping and polyadenylation. Capping is the term used in the art and herein to denote an enzyme-catalyzed reaction between the 5' end of mRNA and m$^7$GTP [7'-methyl guanosinetriphosphate] to generate m$^7$G bound at the 5' end of the mRNA molecule by a unique 5'—5' triphosphate bond. "Capped mRNA" is term for mRNA having a m$^7$GDP covalently bound to the 5'-end of mRNA. The cap structure is m$^7$G(5')ppp(5')N where N is any nucleotide at the 5' end of an RNA. In eukaryotic cells, including human cells, mRNA must be capped in order to be translated efficiently.

Polyadenylation refers to the process of adding varied lengths of polyadenosine (polyA) to the 3'-end of mRNA. Most of the mRNA in a cell is polyadenylated. The standard method used in the art to separate mRNA from other RNA found in eukaryotic cells is to isolate polyadenylated RNA by chromatography through a column of immobilized oligo (U) or oligo(dT). Currently, all cDNA libraries available publicly have been made from polyadenylated mRNA.

The construction of a full-length cDNA library from an mRNA template is a challenging technique for gene structural and functional studies. Conventionally mRNA is purified based on the poly(A)-tail from the 3' end of RNA, and then first-strand cDNA is synthesized using an oligo(dT) primer. Since the mRNAs containing an extensive secondary structure inhibit the progression of reverse transcriptase, this method sometimes produces an incomplete cDNA library. Several methods have been developed to generate a full-length cDNA library. For example, 5' capped mRNA was enriched using chemical introduction of a biotin group to the cap structure or an oligo-capping technique was used in which a synthetic oligonucleotide ligated to the mRNA replaced the cap structure. Other methods used manganese in the reverse transcriptase reaction. The addition of manganese allowed addition of three to four non-templated dCMP residues to the 3' end of full-length cDNA by reverse transcriptase. The cDNA ends were anchored to the double-stranded DNA adaptor. However, all of these methods used poly(A)-tailed mRNA as a starting material for cDNA library construction. Edery et al. (1995) have demonstrated intact and complete capped mRNA isolation using wild-type eIF4E binding to separate eukaryotic mRNA from total RNA using an affinity column.

The term "separable affinity matrix" refers to any material possessing a specific affinity for a ligand and being physically separable from a liquid in which the ligand might be present. Under conditions suitable for binding of the ligand to the separable affinity matrix to occur, the ligand can be purified from the liquid by contacting the liquid containing the ligand with the separable affinity matrix, then separating the matrix from the liquid. The matrix material can be a solid phase material, a gel, or any other type of material capable of being separated by physical, chemical methods or a combination of the two. Commonly used materials include solid phase particles, fibers and continuous surfaces. The specific affinity can be provided by any substance which preferentially binds to a designated ligand. For example, an enzyme can specifically bind its substrate, an antibody can specifically bind its antigen, a receptor can bind its ligand. The choice of matrix material is based on such considerations as the chemical nature of the affinity ligand pair, how readily the matrix can be adapted for the desired specific binding. A separable affinity matrix exemplified herein is composed of agarose beads to which glutathione is covalently bound (glutathione agarose). The ligand which provides specific binding to capped mRNA is a glutathione-S-transferase-eIF4E (GST-4E) fusion protein. The ligand is conveniently bound to the matrix by contacting the solution with glutathione agarose under conditions where binding to GST-4E can occur, then separating the agarose beads from the solution by centrifugation. It will be apparent that other matrix materials, ligand binding pairs and separation methods can be devised, as long as the foregoing principles are followed.

The term "binding" is used herein to include non-covalent binding, without regard to physical mechanism. Such binding is characterized by an equilibrium between bound and unbound states of the ligand. Under conditions where binding can occur, the bound state predominates over the unbound state, at equilibrium. Specific binding is characterized by the fact that the desired ligand is essentially or predominantly the only substance bound. The foregoing use of the term "binding" is that generally understood in the art. The term "affinity-bound" means, in the context herein, specifically bound to a separable affinity matrix.

The present invention is based on a novel method of separating capped mRNA from total RNA of any eukaryotic cell or tissue sample that comprises combining a preparation of RNA containing capped mRNA with a separable affinity matrix having affinity-bound eIF4E, under conditions sufficient for binding of eIF4E to capped mRNA to occur, separating the affinity matrix from the reaction mixture, then separating the capped mRNA from the affinity matrix. The separation can be carried out by column chromatography, or batch-wise, without column chromatography. The process provides a higher yield of mRNA than a conventional method based on isolation of polyadenylated RNA. Data presented herein comparing the two methods demonstrated that mRNA isolated by the method of the invention was 3–5 times more than was isolated by the oligo(dT) method using the same quantity of total RNA starting material. Furthermore, the mRNA prepared by the method of the invention is complete with respect to the 5' end, whereas polyadenylated RNA isolated by an oligo (dT) column is only rarely full length and frequently missing the 5' end, especially of longer mRNAs. Most significantly, the method of the invention isolates a class of mRNA molecules that are not polyadenylated or have poly(A) tails that are not bound effectively to oligo(dT) columns due to inadequate length or other structural characteristics. The method of the invention makes it possible to prepare libraries of mRNA and cDNA containing sequences of expressed genes that have not previously been isolated. The method is therefore of importance for extending genomics and proteomics to include expressed genes and proteins heretofore inaccessible, with mRNA of higher quality than previously available. mRNA isolated according to the invention provides important information regarding transcriptional start site sequence and establishing the correct reading frame for ESTs that lack a complete 5' end.

The eukaryotic initiation factor 4E (eIF4E) is a component of the cellular translational apparatus. Translation initiation on eukaryotic mRNA includes the recruitment of the 40S ribosomal subunit to the 5' end of mRNA. This is mediated by eukaryotic translation initiation complex 4F (eIF4F) that is a heterotrimetic complex containing eIF4E, eIF4A, and eIF4G. eIF4A is an RNA-dependent RNA helicase which unwinds mRNA secondary structure and eIF4G is a large polypeptide containing binding sites for eIF4E, eIF4A, eIF3 and poly(A) binding protein. eIF4E facilitates the initiation of translation by directly binding to the mRNA 5' cap structure ($m^7$GpppN).

The binding of eIF4E to capped mRNA provides the means for isolating capped mRNA from total cell RNA. eIF4E has been cloned, expressed and purified, and is also prepared as a GST fusion protein. In a previous study, we identified four mutants, N118A, K119A, Q120A and W56Y, using alanine mutagenesis of eIF4E S4-H2 loop (Spivak-Kroizman et al., 2001, U.S. Pat. No. 6,232,442) incorporated herein by reference. These mutants had a higher affinity for $m^7$GTP than wild-type eIF4E ($K_d$ of 1.2 $\mu$M for wild-type as compared to 0.1 $\mu$M to <0.03 $\mu$M for mutants). Although mRNA can be isolated using wild-type eIF4E, the high affinity mutants are preferred. The K119A mutant (U.S. Pat. No. 6,232,442) was used for the studies described herein, although other versions of eIF4E having affinity for m7GTP greater than wild-type can also be employed. The affinity of eIF4E for $m^7$GTP is expressed herein as a dissociation constant, $K_d$. The higher the affinity, the smaller the dissociation constant. The use of high affinity mutants has made it possible to conduct batch-wise purification, without resorting to column chromatography. Batch-wise purification is both simpler and less costly, yet the yield of full length mRNA is greater than obtainable by the oligo(dT) method.

A high affinity eIF4E is herein defined as one having at least two-fold difference in $K_d$ compared to wild-type eIF4E when directly compared by the same measurement technique. Numerical values for $K_d$ will vary depending upon the assay procedure and assay conditions. The term "high affinity" is based on measurements of $K_d$ by changes in intrinsic protein fluorescence as described by Hsu, P-C, et al. (2000) Biochemistry 39:13730–13736, incorporated herein by reference. See also U.S. Pat. No. 6,232,442. Briefly, eIF4E binding assays were performed in a buffer of 20 mM HEPES (pH 7.6) and 1 mM DTT. Fluorescence measurements were made at 25° C. on a SPEX Fluorolog-T2 spectrofluorometer equipted with a high intensity (450 w) xeron arc lamp. An excitation wavelength of 280 nm was used to monitor the tryptophan fluorescence emission of recombinant eIF4E at 330 nm. Excitation and emission slit widths of 1.4 and 2.0 mm respectively were used and a 1.0 cm sample cell pathlength was employed. The steady state data were collected and analyzed according to the art-known methods. In these assays, the changes in the intrinsic fluorescence of the proteins were observed with the addition of $m^7$GTP.

The work reported herein was carried out using human eIF4E and mutants thereof. The term "wild-type" eIF4E refers specifically to that abundant form of human eIF4E previously isolated and characterized (U.S. Pat. No. 6,232,442). The known eIF4Es of other species are structurally similar to that of human; however, the possibility exists of high-affinity eIF4E isoforms of human or other species. There may even be isoforms that meet the disclosed criteria for high affinity eIF4E. Although the high affinity variants of eIF4E described herein are mutants, it will be understood that the term "high affinity" eIF4E is not intended to exclude naturally occurring variants of eIF4F of human or non-human origin.

The novel high affinity mutant W56Y was shown therein to have a $K_d$ of 0.11 $\mu$M compared with 0.3176 $\mu$M for wild-type, and is therefore suitable for use in the process of the invention. W56Y was made according to techniques described in U.S. Pat. No. 6,232,442, and Hsu, P-C et al., (2000).

All of the eIF4Es employed herein were expressed and purified as fusion proteins having glutathione-S-transferase (GST) fused to the $NH_2$ end of eIF4E. The fusion of GST to eIF4E did not interfere with binding to $m^7$GDP, $m^7$GTP or to capped mRNA, nor did it interfere with binding GST to glutathione. Conveniently, the GST-eIF4E (GST-4E) fusion could be readily bound to glutathione-agarose, which is commercially available, thereby providing a separable affinity matrix for binding and separating capped mRNA from an RNA mixture. Binding to glutathione-agarose occurs through the GST moiety of the fusion protein so that the cap binding site is oriented away from the agarose bead, which facilitates binding capped mRNA.

The conditions for binding to occur, and for the mRNA preparation in general, are essentially those which are understood in the art to apply to biological materials. For example it is essential to avoid conditions that are known to degrade RNA, denature protein, or disrupt specific protein-ligand binding interactions. Optimum results are achieved by selecting conditions that maximize the desired specific binding reactions and minimize non-specific binding. Denaturing the RNA prior to binding improves yield by reducing secondary structure of the RNA that could mask the 5' cap site. The binding reaction is not especially sensitive to ionic strength and can be carried out with total salt concentrations in the range of 50 mM to 500 mM. The binding reaction can be carried out at a convenient temperature from 40° C. to at least room temperature. The use of a carrier material is necessary to prevent non-specific binding of mRNA to the matrix material, e.g. agarose beads, or to the container walls. Various carrier materials are known in the art, although materials of a defined molecular size are preferred. Transfer RNA (tRNA) is exemplified herein but other materials, such as linear acrylamides of defined lengths, can be employed. The use of non-stick, hydrophobic surfaced test tubes is recommended, to minimize non-specific attachment of RNA to vessel walls. The separable affinity matrix is mixed gently with the mRNA solution, for example by end-over-end mixing. More vigorous mixing, such as vortexing, should be avoided. The affinity matrix is conveniently separated from the reaction mixture by brief centrifugation, followed by a series of washes by resuspending in wash solution and again separating by centrifugation. Washing with buffer containing GDP, or a mixture of nucleotide triphosphates is useful to reduce any binding that is not cap-specific. (See FIG. 3). Additional components of the binding buffer are provided to reduce RNAse or protease activity or to minimize non-specific binding.

Separating the bound, capped mRNA from the affinity matrix was carried out initially by elution with an excess of $m^7GDP$. More mRNA was removed by acid phenol/chloroform extraction. The latter step could be used as a single separation step to remove capped mRNA from the matrix. Other methods for separating mRNA from the matrix will be apparent to those skilled in the art.

The isolated mRNA can be used in a variety of ways, some of which are similar to those uses already known for mRNA prepared by the oligo(dT) method, while others take advantage of unique properties of the mRNA prepared by the method of the invention. The method of the invention provides an mRNA library which can be used to prepare a cDNA library by well-known conventional methods using reverse transcription and DNA polymerase reactions. Molecules of double-stranded cDNA in the library will have one strand of complementary sequence to the capped mRNA sequences, as is known in the art. Libraries produced by the invention have a higher proportion of full-length sequences and also of cDNA coding for NH2-terminal sequences. A library composed almost entirely of full length cDNA can be readily prepared by removing any partial length heteroduplexes cRNA:DNA hybrids using a single-strand specific ribo-nuclease, full length heteroduplexes retaining the 5' cap, can be re-isolated using high-affinity eIF4E beads, thereby enriching for full length heteroduplexes. Direct expression and full length sequencing of genes in the library are greatly facilitated using a library of the invention. In addition, it has been shown herein that the method of the invention provides mRNA sequences that are not isolated by the conventional method. Therefore the libraries of the invention include sequences not found in currently available libraries.

The invention also provides new opportunities for diagnostic tests, based on the presence of capped mRNA in a biological or clinical cell sample. There are many pathological conditions that can be characterized by the presence in a cell of novel, or elevated level of, capped mRNA. For example virus infection can be diagnosed by detecting the presence of capped viral RNA, which is often not polyadenylated. The convenience provided by the batchwise separation makes the diagnosis by differential gene expression a simpler and commercially feasible process. Accordingly, total capped mRNA can be separated from the RNA of the cells having the pathologic condition, and the presence or amount of the designated or diagnostic mRNA identified. The designated mRNA is one whose presence, or altered amount is considered to be an indicator of the pathologic condition. Where the designated mRNA is not polyadenylated, the capped mRNA can be further purified by removing polyadenylated RNA using a conventional oligo(dT) column. Designated mRNA can be identified by a labeled probe that binds to a unique or characteristic sequence of the designated mRNA. A variety of fluorescent, luminescent or radioactive probes are known in the art. Alternatively, the designated mRNA, or a unique segment thereof, can be amplified using polymerase chain reaction and subsequently characterized by known methods of probing and/or hybridization. By comparison with the result observed with normal control cells, the presence and, if desired, relative amount of the designated mRNA can be identified. The method can be adapted with the use of multi-well plates, membranes or glass arrays to evaluate the presence and/or amount of a plurality of designated mRNAs, to achieve a differential diagnosis of virus infection, or to evaluate patterns of gene expression in, e.g., tumor tissue or other complex conditions such as HCV infection or HIV infection. The results of such evaluation can be valuable for choosing an appropriate course of therapy, or for evaluating disease prognosis

EXAMPLES

Example 1

Rapid Isolation of mRNA by Batch Binding with GST-4E.

Glutathione agarose beads (Sigma, St. Louis, Mo.) were hydrated with diethyl pyrocarbonate (DEPC)-treated water for 2 hr at room temperature. The beads (1 ml, packed volume) were mixed with FPLC purified GST-4E protein (2.8 mg) in PBS buffer for 1 hr at 4° C. for 10 min) were mixed and added 200 µl of 1X mRNA binding buffer (BB) (10 mM $KHPO_4$ [pH 8.0], 100 mM KCl, 2 mM EDTA, 5% glycerol, 100 µg/ml bovine liver tRNA (Sigma, St. Louis, Mo.), 6 mM dithiothreitol, 1.3% polyvinyl alcohol (Sigma, St. Louis, Mo.), 0.005% TritonX-100, 20 U RNasin [Roche, Basel, Switzerland]). The incubation was performed for 1 hr in a 1.5 nonstick hydrophobic microfuge tube (Gene Mate). Following end-over-end mixing at room temperature, the resin was washed twice with 1 ml of 1X binding buffer and three times with 1 ml of 1X binding buffer containing either 500 1 µM GDP. mRNA was specifically eluted with 1 ml or less 1X binding buffer containing 1 mM $m^7GDP$. The remaining mRNA that was bound to beads was extracted with an equal volume of acid phenol/chloroform (Ambion, Austin, Tex.). Each fraction was collected and precipitated with glycogen (10 µg), 3M sodium acetate, and ethanol. RNAs were analyzed by 7M urea-polyacrylamide (6%) gel electrophoresis.

Comparison of Ability of GST-4E$_{wild-type}$ and GST-4E$_{K119A}$ to Isolate 5' Capped mRNA.

Figure 1B:
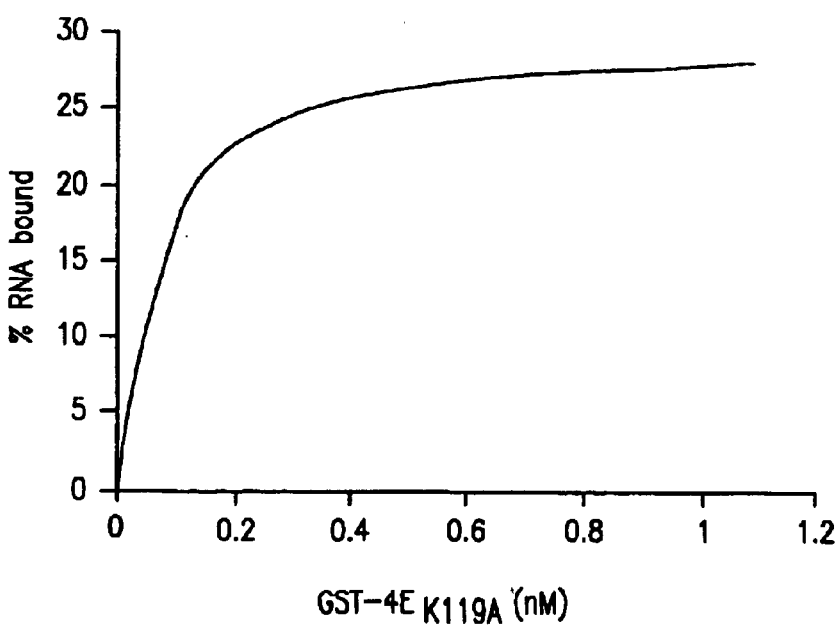
FIG. 1B is a graph of mRNA binding by the high-affinity mutant, GST-eIF4E$_{K119A}$ fusion protein.

Batch mRNA binding assays were performed to compare binding affinities of GST-4E$_{wild-type}$ and GST-4E$_{K119A}$. 5' capped $^{32}P$-labeled mRNA was incubated with increasing amounts of GST-4E$_{wild-type}$ (Panel A) and GST-4E$_{K119A}$ bound to agarose beads (Panel B) as described. The quantities of mRNA bound to GST-4E agarose beads were determined by measuring Cerenkov counts. The dissociation constant ($K_d$) of GST-4E$_{wild-type}$ and GST-4E$_{K119A}$ were 0.15 nM and 0.06 nM for capped mRNA, respectively. The $K_d$ values were calculated as described previously (Weeks and Crothers, 1992). The results are shown in FIG. 1A and FIG. 1B.

Example 2

Specificity of GST-4E$_{K119A}$ for 5' Capped mRNA.

Figure 2A:
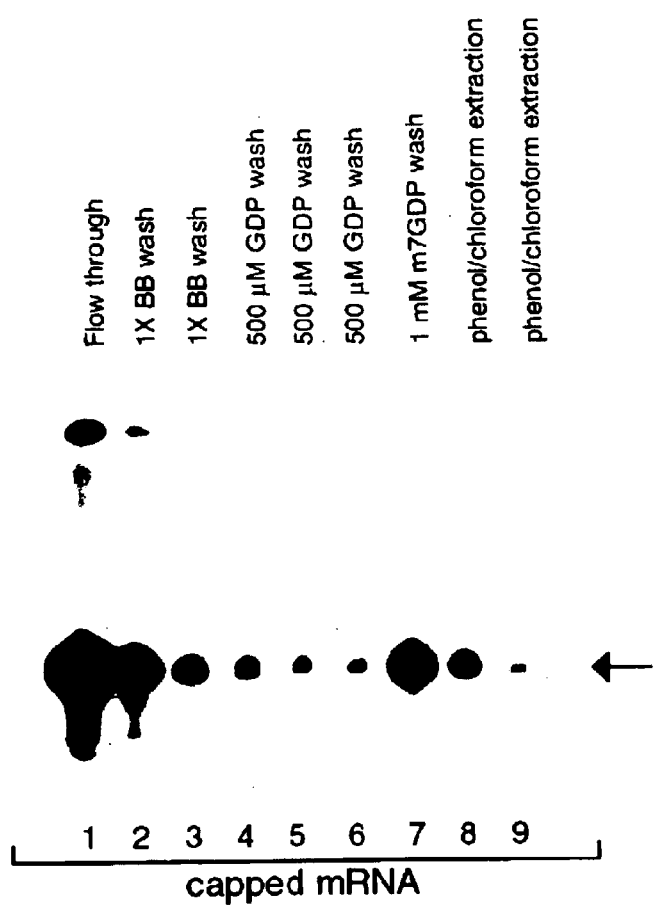
FIG. 2A shows polyacrylamide gel electrophoresis of a labeled mRNA preparation containing capped mRNA, showing the products of stages of the purification process, as indicated.
Figure 2B:
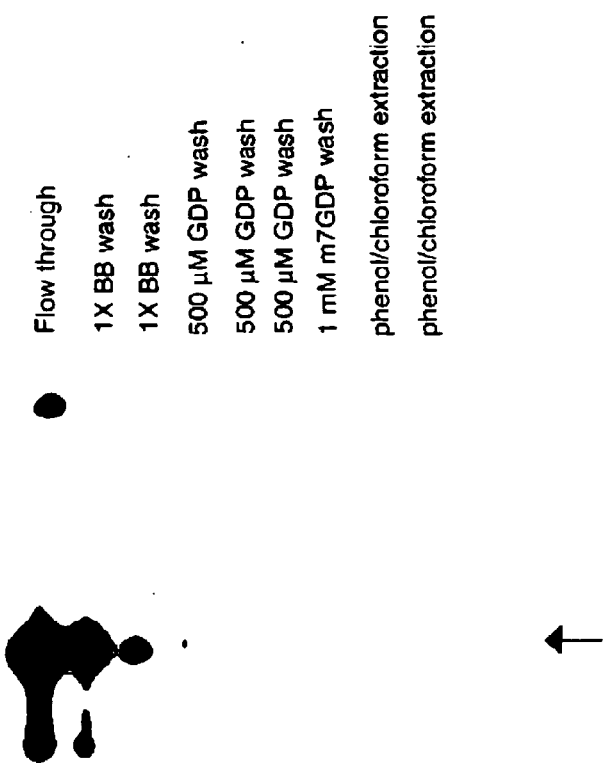
FIG. 2B shows polyacrylamide gel electrophoresis of a labeled, un-capped mRNA preparation, at stages of the purification process, as indicated.

The rapid batch purification of mRNA using GST-4E$_{K119A}$ was tested for its ability to bind both 5' capped and uncapped mRNAs. Both 5' capped and uncapped mRNAs synthesized in vitro using T7 polymerase were mixed with GST-4E$_{K119A}$ agarose beads, washed with 1X binding buffer, and 500 µM GDP and eluted with 1 mM m$^7$GDP as described in Example 1. mRNA that remained bound to GST-4E despite the m$^7$GDP elution step was recovered by extraction with acid phenol/chloroform. mRNA present in different purification stages using GST-4E$_{K119A}$ agarose beads are shown for 5' capped (FIG. 2A) and uncapped mRNA (FIG. 2B). mRNA present in each sample was precipitated with ethanol and analyzed by 8 M urea-polyacrylamide (6%) gel electrophoresis. The arrow indicates the size of full-length mRNA (50 nt) used as a starting material.

Example 3
The Purification of Native Functional mRNA from Total Human Liver RNA Using GST-4E$_{K119A}$ in a Batch Method and Oligo(dT) in a Column Method.

Figure 3A:
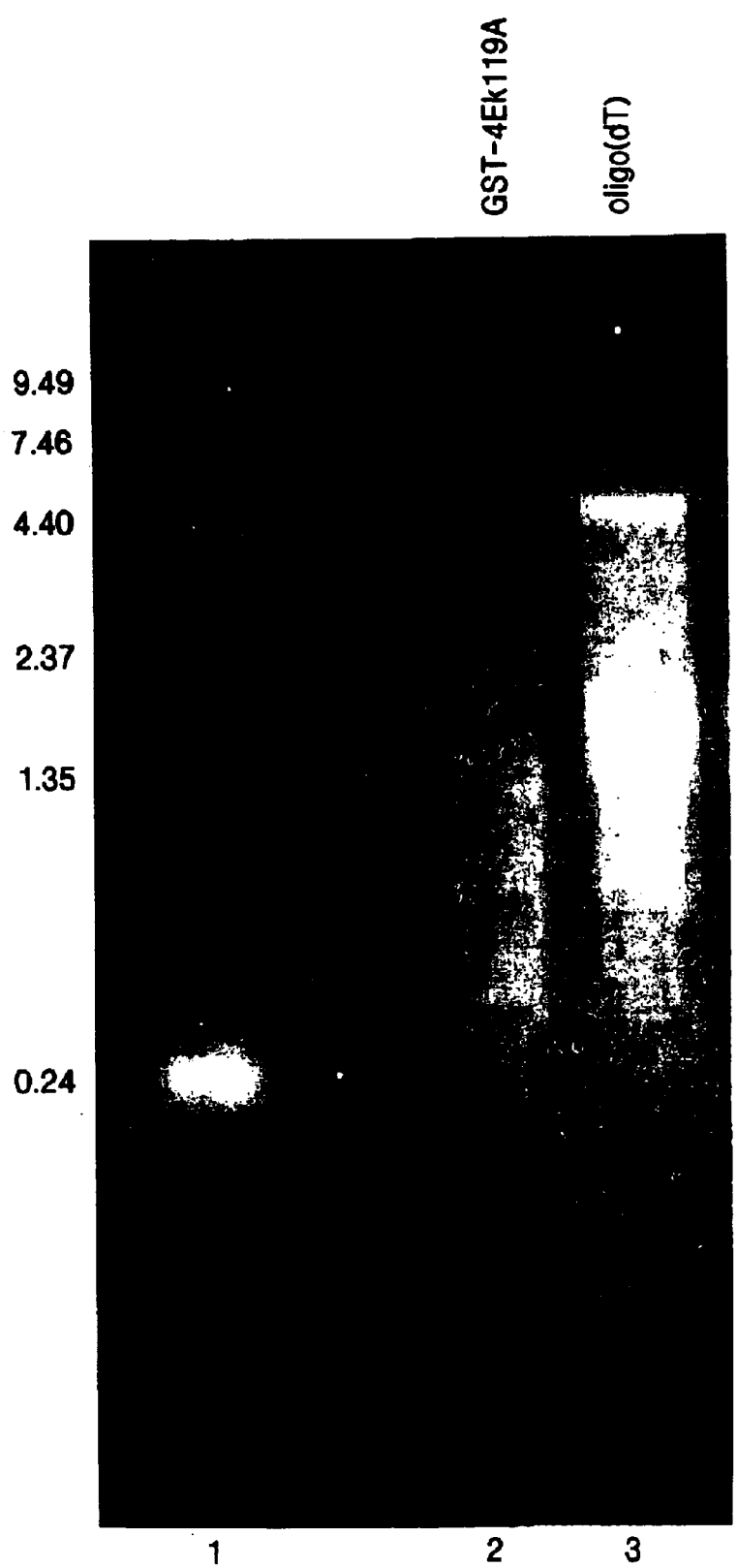
FIG. 3A is a print of gel electrophoresis of mRNA prepared either by the method of the invention (lane 2) or by a standard oligo(dT) method (lane 3). Lane 1 is a set of size standards (Kb).

Five hundred (500) µg of total RNA from normal or HCV-infected liver was mixed with either GST-4E$_{K119A}$ or applied to an oligo(dC$_{10}$T$_{30}$) column. Agarose beads linked to GST-4E$_{K119A}$ (200 µl packed volume) were incubated with total RNA in 500 µl 1X binding buffer for 1 hr at room temperature. The beads were washed twice with 1 ml 1X binding buffer and three times with 1X binding buffer containing 500 µM GDP as described in Example 1. mRNA was recovered by directly extracting beads with acid phenol/chloroform. The mRNA recovered was precipitated in the presence of glycogen and ethanol. Poly(A)-tailed mRNA was purified as suggested by the manufacturer using oligotex (QIAGEN™, Valencia, Calif.). 30% of the mRNA recovered from each sample using either GST-4E$_{K119A}$ or oligo (dT) was analyzed by 1% formaldehyde agarose gel electrophoresis. FIG. 3A: mRNA analysis by denaturing agarose gel electrophoresis. Lane 1:0.24–9.5 Kb RNA ladder; lane 2, batch purification of mRNA from normal liver using GST-eIF4E$_{K119A}$ agarose beads; lane 3, mRNA purified from normal liver using an oligo (dT) column. FIG. 3B: Yield and % recovery for rapid batch purification of 5' capped mRNA from total liver RNA.

Figure 4:
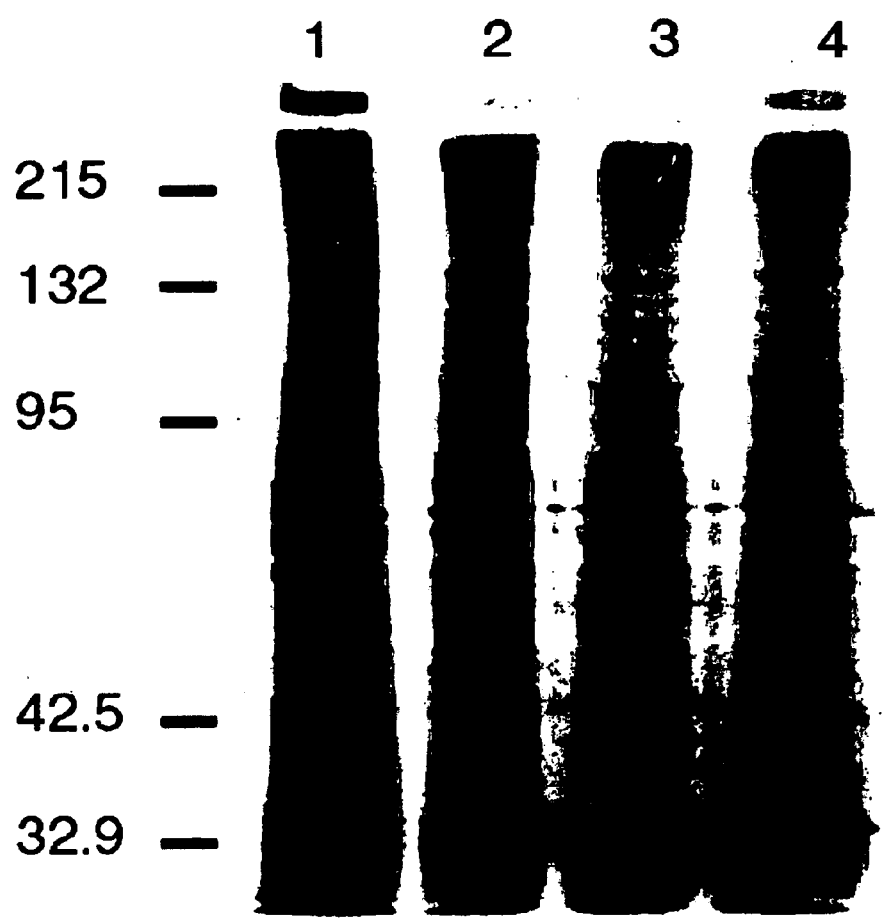
FIG. 4 is a set of electrophoretic gels of proteins translated from mRNA from: Lane 1, normal liver mRNA purified with GST-4E$_{K119A}$ (5'-cap selected), Lane 2, normal liver mRNA purified with oligo(dT) (polyA selected), Lane 3, Hepatitis C virus (HCV) infected liver mRNA 5'-cap selected, Lane 4, HCV-infected liver mRNA polyA selected.

Example 4
In vitro Translation of mRNAs Purified Using GST-4E$_{K119A}$ or Oligo(dT).

mRNA (1 µg) isolated by either the GST-4E$_{K119A}$ batch and oligo(dT) column methods were translated in rabbit rectculocyte lysates with ($^{35}$S) methione. Protein products were analyzed by 10% SDS-PAGE and autoradiography. See FIG. 4: Lane 1; proteins synthesized from normal liver mRNA purified with GST-4E$_{K119A}$ (5' cap selected); lane 2; proteins synthesized from normal liver mRNA purified with oligo(dT) (poly (A) selected); lane 3, proteins synthesized from HCV-infected liver mRNA purified with GST-4E$_{K119A}$; lane 4, proteins synthesized from HCV-infected liver mRNA with oligo(dT). Molecular mass standards were shown in lane 1.

Example 5
Preparation of cRNA.

Six normal liver tissues were used to extract total RNA by TRI reagent (Molecular Research Center, Cincinnati, Ohio). Approximately 20 µg of total RNA or 5 µg of mRNA (5' capped or poly(A)-tailed) was used to synthesize cDNA using Superscript II RT for 1 hr at 42° C. with oligo(dT)$_{24}$ primer containing a T7 RNA polymerase promoter at the 3' of the primer and then cDNA was used as template for double stranded cDNA synthesis using E. coli DNA polymerase, E. coli DNA ligase, and T4 DNA polymerase at 16° C. for 2 hr. Synthesis of cRNA was performed using T7 RNA polymerase as described in the manufacturer's protocol (Enzo Diagnostics, Inc., Farmingdale, N.Y.). The biotin-labeled cRNA was purified using RNeasy spin column (Qiagen®, Valencia, Calif.). Twenty micrograms of cRNA were fragmented with fragmentation buffer (40 mM Tris-acetate, pH 8.1, 100 mM potassium acetate, 30 mM magnesium acetate) at 94° C. for 35 min.

Comparison of Gene Profiles in the 5' Cap Selected and Poly (A) Selected mRNAs Using Oligonucleotide Array Hybridization.

Figure 5:
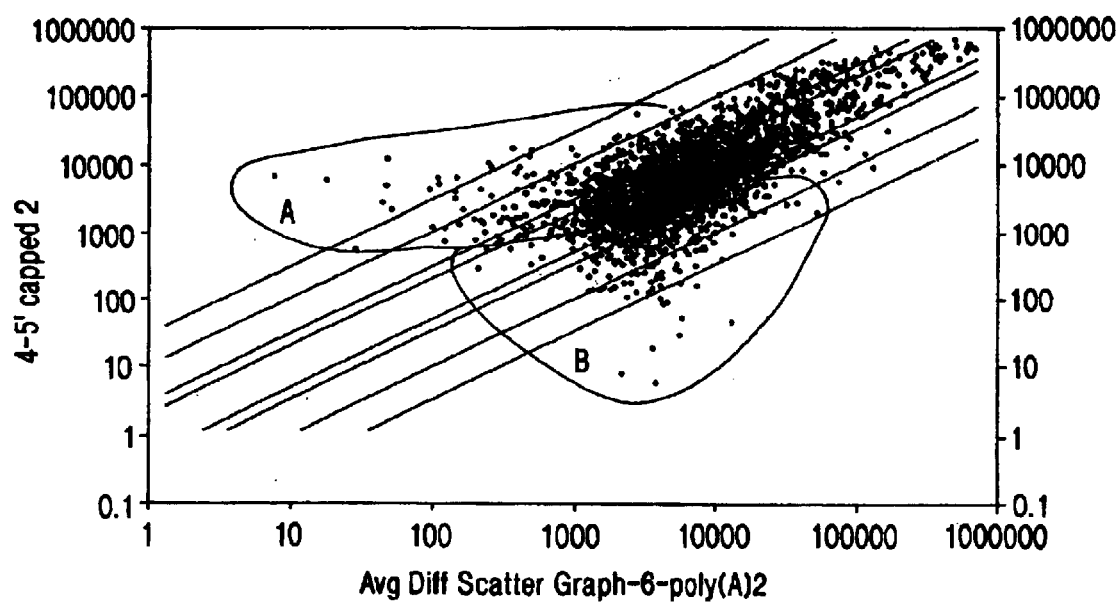
FIG. 5 is a plot of mRNAs selected and quantitated using oligonucleotide arrays and a Gene Chip Scanner. Each dot represents a different mRNA hybridizing to a different EST or gene fragment on the chip. Red dots are RNAs isolated by both oligo(dT) and eIF4E. The dotted area labeled B is occupied by RNAs isolated only by oligo(dT). Area A dots are RNAs isolated by high affinity eIF4E binding to capped mRNA. The remaining dots represent RNAs isolated by both oligo(dT) and by eIF4E.

Purified mRNAs were used as template for preparation of cDNA and double-stranded cDNA synthesis. Then, biotin-labeled cRNA was generated as described and hybridized to the array. The array was read using a Gene Chip (Affymatrix HGU95AV2) scanned using a Hewlett-Packard G2500A Gene Assay Scanner. The results are shown in FIG. 5. Each dot represents an individual mRNA. mRNAs in area A were isolated only by eIF4E binding; area B dots were mRNAs isolated only by oligo(dT). All others were isolated by both methods, although individual capped, non-polyadenylated mRNAs probably exist outside the A area. The results demonstrate the existence of substantial numbers of capped mRNAs that are not polyadenylated.

What is claimed is:

1. A process for preparing capped mRNA from a RNA mixture comprising the steps of combining in a reaction mixture the RNA mixture containing capped mRNA with an affinity matrix having a high-affinity eIF4E mutant bound thereto, wherein the high-affinity eIF4E mutant has a Kd of at least two fold lower than that of the wild type eIF4E and comprises a mutation selected from the group consisting of N118A, K119A, Q120A and W56Y, under conditions sufficient for binding to occur between the high-affinity eIF4E mutant and the capped mRNA, whereby capped mRNA is bound to the affinity matrix, separating the affinity matrix from the reaction mixture, then separating the capped mRNA from the affinity matrix, whereby the capped mRNA is prepared.

2. The process of claim 1 comprising the added step of denaturing the RNA prior to combining with the affinity matrix.

3. The process of claim 1 wherein the affinity matrix consists essentially of glutathione-agarose beads having glutathione-S-transferase-high-affinity eIF4E mutant fusion protein bound thereto.

4. The process of claim 1 wherein the capped mRNA bound to the affinity matrix is separated therefrom by eluting with m$^7$GDP or m$^7$GTP.

5. The process of claim 1 wherein the capped mRNA bound to the affinity matrix is separated therefrom by extraction with phenol/chloroform.

* * * * *